(12) United States Patent
Lin

(10) Patent No.: US 8,987,890 B1
(45) Date of Patent: Mar. 24, 2015

(54) FLEXIBLE CHIP SET ENCAPSULATION STRUCTURE

(71) Applicant: Ghi Fu Technology Co., Ltd., Chang Hua County (TW)

(72) Inventor: Li-Chi Lin, Chang Hua County (TW)

(73) Assignee: Ghi Fu Technology Co., Ltd., Chang Hua County (TW)

( * ) Notice: Subject to any disclaimer, the term of this patent is extended or adjusted under 35 U.S.C. 154(b) by 0 days.

(21) Appl. No.: 14/022,420

(22) Filed: Sep. 10, 2013

(51) Int. Cl.
*H01L 23/48* (2006.01)
*H01L 23/31* (2006.01)

(52) U.S. Cl.
CPC .................... *H01L 23/3114* (2013.01)
USPC .......................................... 257/696; 257/692

(58) Field of Classification Search
USPC ................................. 257/692, 696
See application file for complete search history.

(56) References Cited

U.S. PATENT DOCUMENTS 7,787,254 B2 * 8/2010 Clayton et al. ................ 361/749

* cited by examiner

*Primary Examiner* — Quoc Hoang
(74) *Attorney, Agent, or Firm* — Ming Chow; Sinorica, LLC

(57) ABSTRACT

A flexible chip set encapsulation structure includes a chip set. The chip set comprises a plurality of spaced chips and a fixing film. The fixing film is adapted to wrap and fix the chips. The fixing film has at least one bending portion at a predetermined position for the fixing film to have flexibility in a predetermined direction. Thus, the flexible chip set encapsulation structure is flexible for bending. When the user wears the flexible chip set, the movement of the user won't be confined. Besides, the chip set is completely attached to the body to provide a comfortable wear, and the chips provide a better far infrared radiation effect.

6 Claims, 14 Drawing Sheets

FLEXIBLE CHIP SET ENCAPSULATION STRUCTURE

BACKGROUND OF THE INVENTION

1. Field of the Invention

The present invention relates to a flexible chip set encapsulation structure.

2. Description of the Prior Art

FIG. 1 is a perspective view of a conventional chip set encapsulation structure. The chip set encapsulation structure comprises a fixing film 1. The fixing film 1 wraps a plurality of chips 2 to constitute a chip set 3. When the chip set 3 is attached to the user's body, the chip set 3 will irradiate far infrared to the user. The far infrared can emit micro energy to the user. The micro energy is absorbed by the user's water molecules through resonance absorption to generate angle vibration so as to promote blood circulation and to enhance metabolism. The large water molecule is decomposed to small water molecule. The chip set also provides sterilization and deodorization effects.

However, the flexibility of the fixing film 1 of the conventional chip set encapsulation structure is not good and the chip set 3 cannot be curved at a large angel freely. When the chip set 3 is used, the use's movement is confined and the user cannot bend freely. The chip set 3 cannot be attached to the user's body completely to cause uncomfortable wear. Accordingly, the inventor of the present invention has devoted himself based on his many years of practical experiences to solve these problems.

SUMMARY OF THE INVENTION

The primary object of the present invention is to provide a flexible chip set encapsulation structure having good flexibility. The flexible chip set encapsulation structure can be bent freely, not confining movement of the user, and it is completely attached to the use's body to enhance the comfortable wear.

In order to achieve the aforesaid object, the flexible chip set encapsulation structure of the present invention comprises a chip set. The chip set comprises a plurality of spaced chips and a fixing film. The fixing film is adapted to wrap and fix the chips. The fixing film has at least one bending portion at a predetermined position for the fixing film to have flexibility in a predetermined direction.

Through the bending portion, the fixing film can be bent freely to form a flexible chip set having a good flexibility. When the user wears the flexible chip set, the user can bend freely, not limited to the flexible chip set encapsulation structure. The chip set is completely attached to the user's body. This provides a comfortable wear, and the chips provide a better far infrared radiation effect.

DETAILED DESCRIPTION OF THE PREFERRED EMBODIMENTS

Embodiments of the present invention will now be described, by way of example only, with reference to the accompanying drawings.

Figure 1:
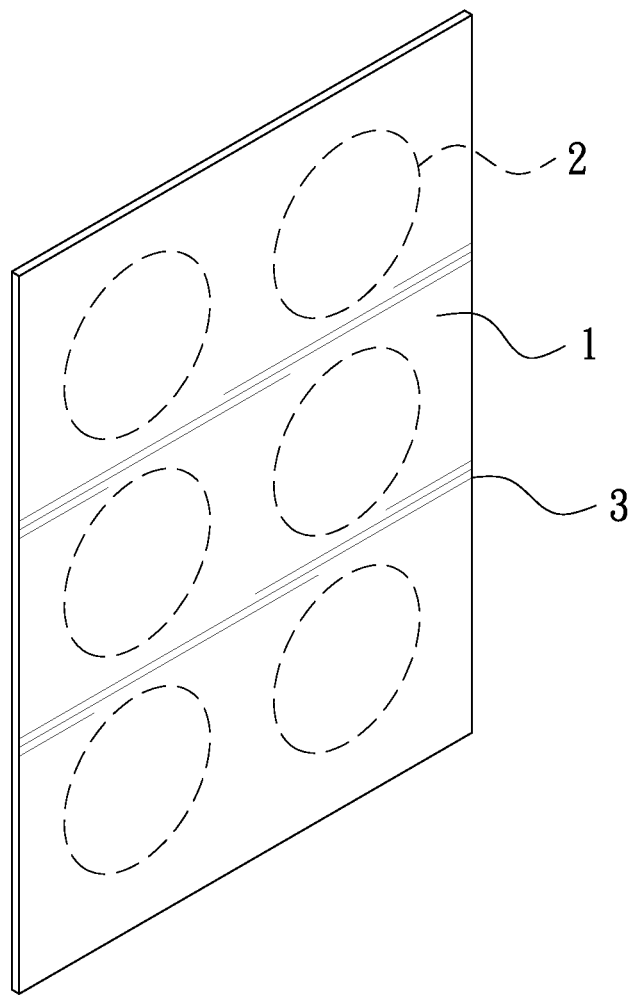
FIG. 1 is a perspective view of a conventional chip set encapsulation structure.
Figure 2:
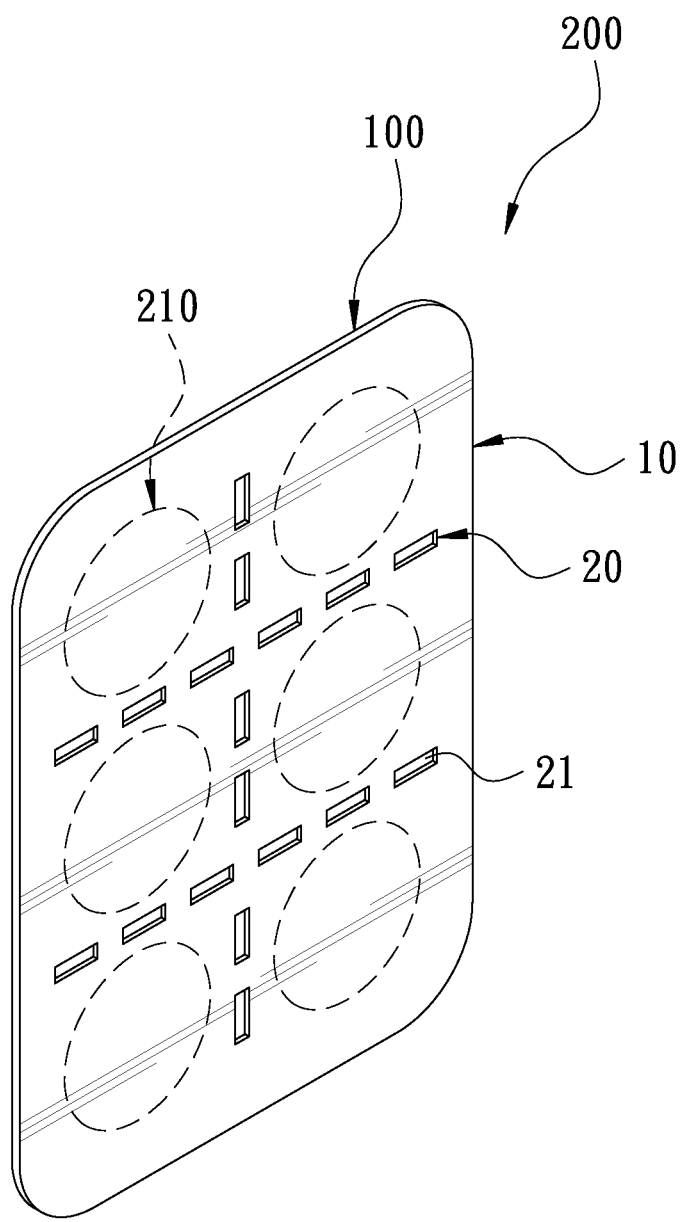
FIG. 2 is a perspective view according to a first embodiment of the present invention.

FIG. 2 is a perspective view according to a first embodiment of the present invention. The present invention discloses a flexible chip set encapsulation structure 100. The flexible chip set encapsulation structure 100 comprises a chip set 200. The chip set 200 comprises a plurality of chips 210 spaced and arranged at a predetermined position and a fixing film 10. The fixing film 10 is adapted to wrap and fix the chips 210, so that the chips 210 can be separately confined and fixed in the fixing film 10. In the first embodiment of the present invention, the fixing film 10 is made of a flexible EVA material, but not limited to this material. The fixing film 10 can be made of PE, TPR, TPU or the like material. The fixing film 10 has a plurality of bending portions 20 at a predetermined position. The bending portions 20 are disposed along the vertical direction and the transverse direction of the fixing film 10, and staggered and spaced at the predetermined position of the fixing film 10. The bending portions 20 are disposed at the relative position between the chips 210 of the fixing film 10. In the first embodiment of the present invention, the bending portions 20 are a plurality of spaced recesses 21 for the fixing film 10 to be bent flexibly, so that the fixing film 10 is flexible in a predetermined direction and the fixing film 10 can be bent freely at the position of the bending portions 20.

Figure 3:
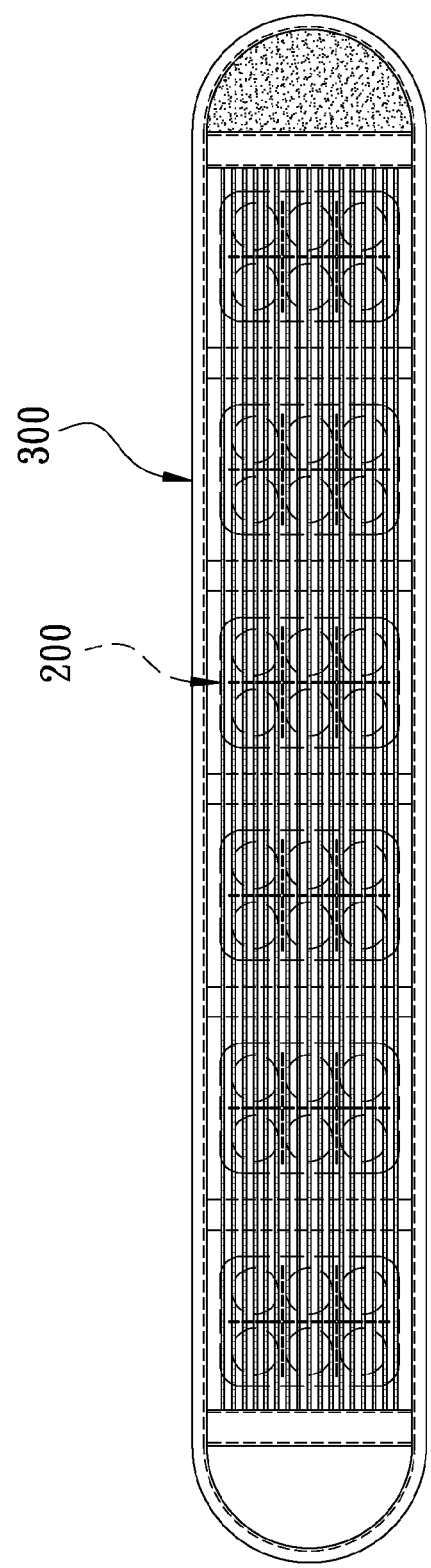
FIG. 3 is a schematic view of the first embodiment of the present invention when in use.
Figure 4:
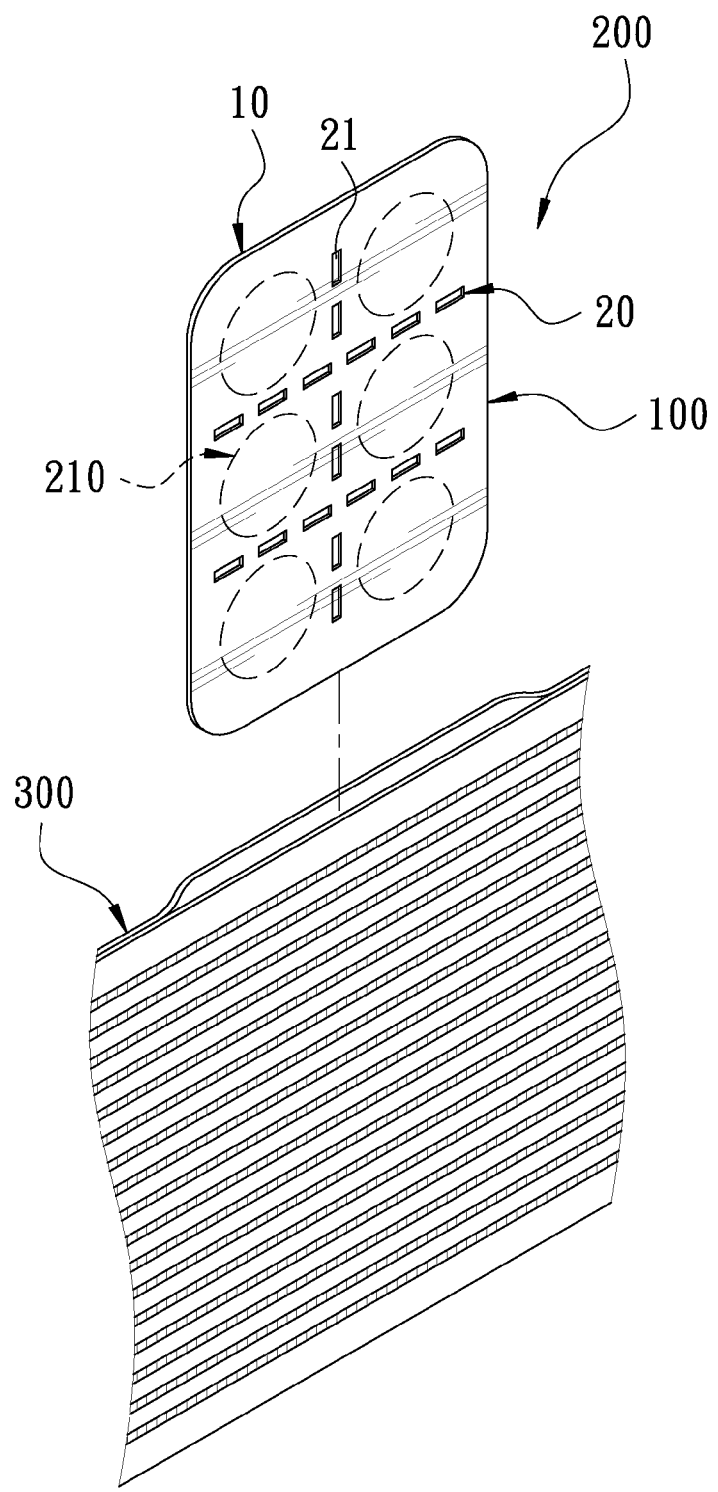
FIG. 4 is an exploded view according to the first embodiment of the present invention.
Figure 5:
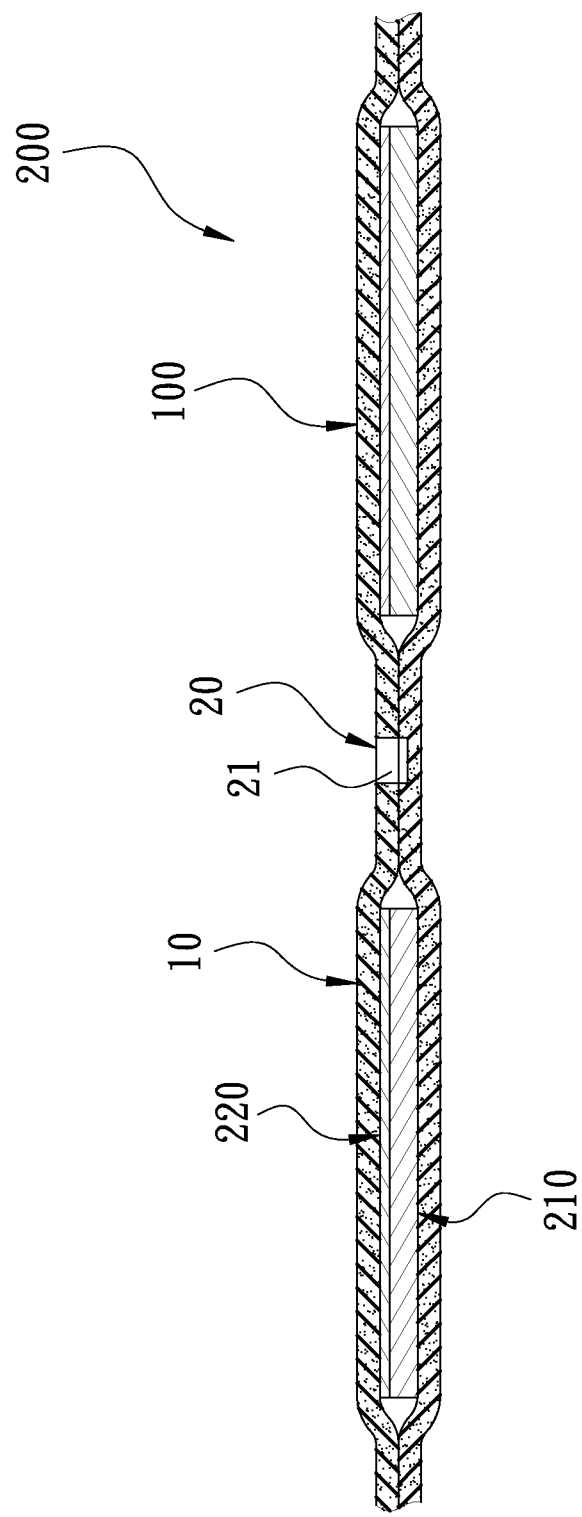
FIG. 5 is a sectional view according to the first embodiment of the present invention.

Referring to FIG. 3 to FIG. 5, the chip set 200 is placed in a telescopic belt 300. One side of the chips 210 is coated with an energy coating 220. The material of the energy coating 220 comprises copper, carbon, silicon, manganese, phosphorus, sulfur, nickel, germanium, chromium, molybdenum, titanium, vanadium and so on which are mixed in a ratio for the energy coating 220 to radiate far infrared radiation energy. In the first embodiment of the present invention, the bending portions 20 are disposed along the long axis and the short axis of the telescopic belt 300 and spaced at the predetermined position of the fixing film 10. The bending portions 20 are disposed at the relative position between the chips 210 of the fixing film 10, so that the fixing film 10 is flexible along the long axis and the short axis of the telescopic belt 300 and the chip set 200 is flexible freely along with the telescopic belt 300.

Figure 6:
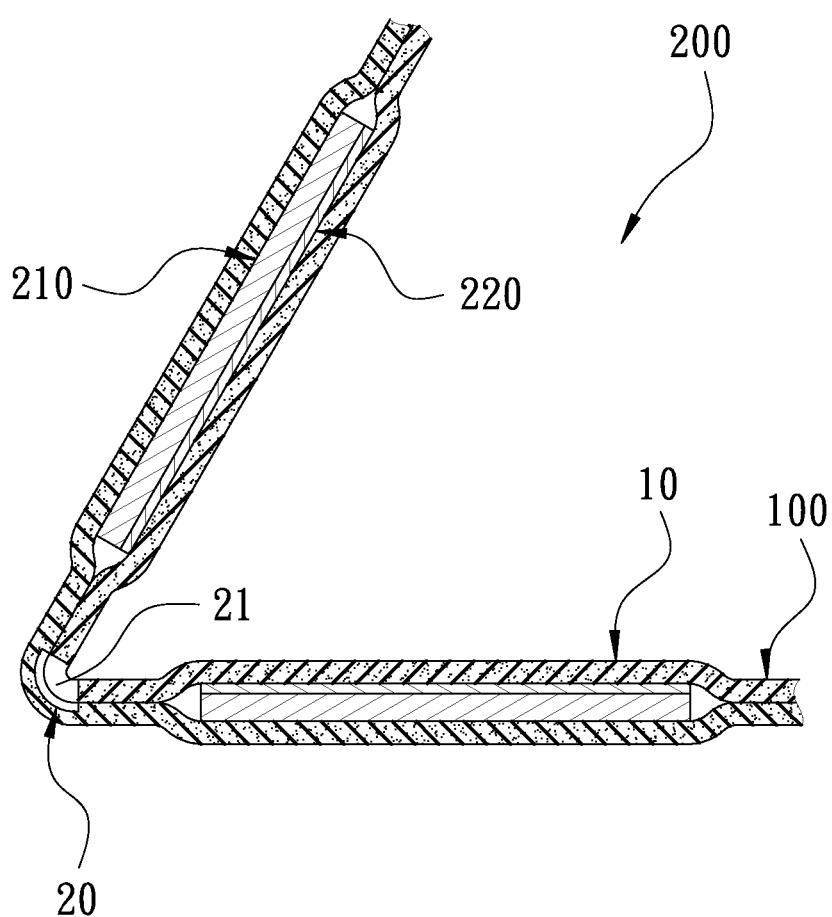
FIG. 6 is a sectional view according to the first embodiment of the present invention in a curved state.

Referring to FIG. 5, FIG. 6 and FIG. 3, the flexible chip set encapsulation structure 100 has a flexible and curved space through the bending portions 20. The fixing film 10 has the property of flexibility in the predetermined direction for the flexible chip set encapsulation structure 100 to be bent at a large angle, so that the chip set 200 has a good flexibility to be curved freely. The chip set 200 becomes a flexible chip set to be curved freely along with the telescopic belt 300. Thus, when the chip set 200 cooperates with the telescopic belt 300 to wrap the waist of the user, the waist of the user is free to bend and move, not limited by the flexible chip set encapsulation structure 100. Through the bending portions 20, the chip set 200 can be completely attached to the body along with the flexibility of the telescopic belt 300. This provides a comfortable wear, and the chips 210 abut against the body to provide a better far infrared radiation effect.

Figure 7:
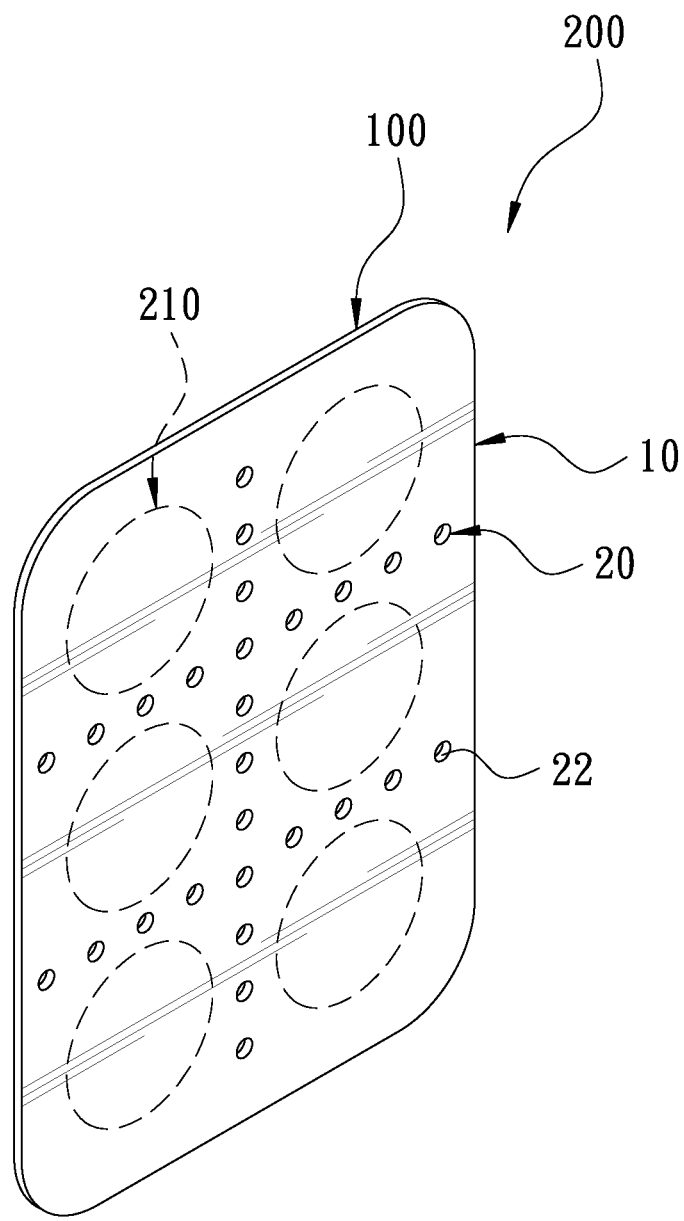
FIG. 7 is a perspective view according to a second embodiment of the present invention.
Figure 8:
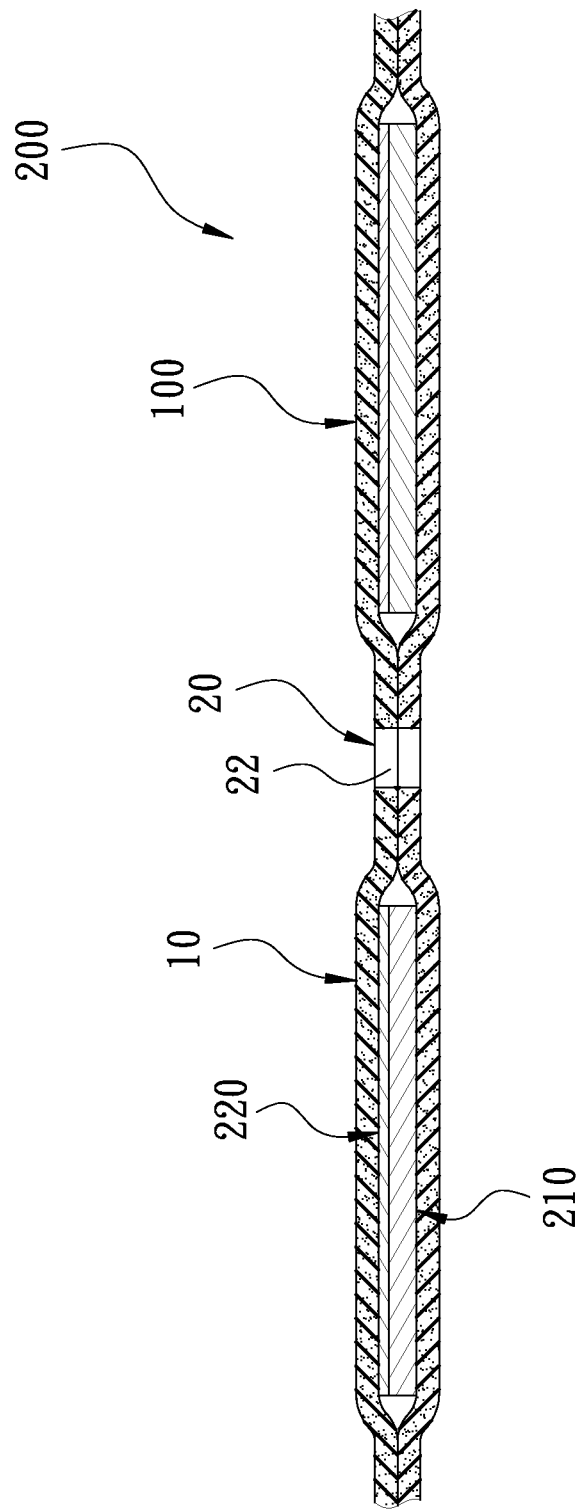
FIG. 8 is a sectional view according to the second embodiment of the present invention.
Figure 9:
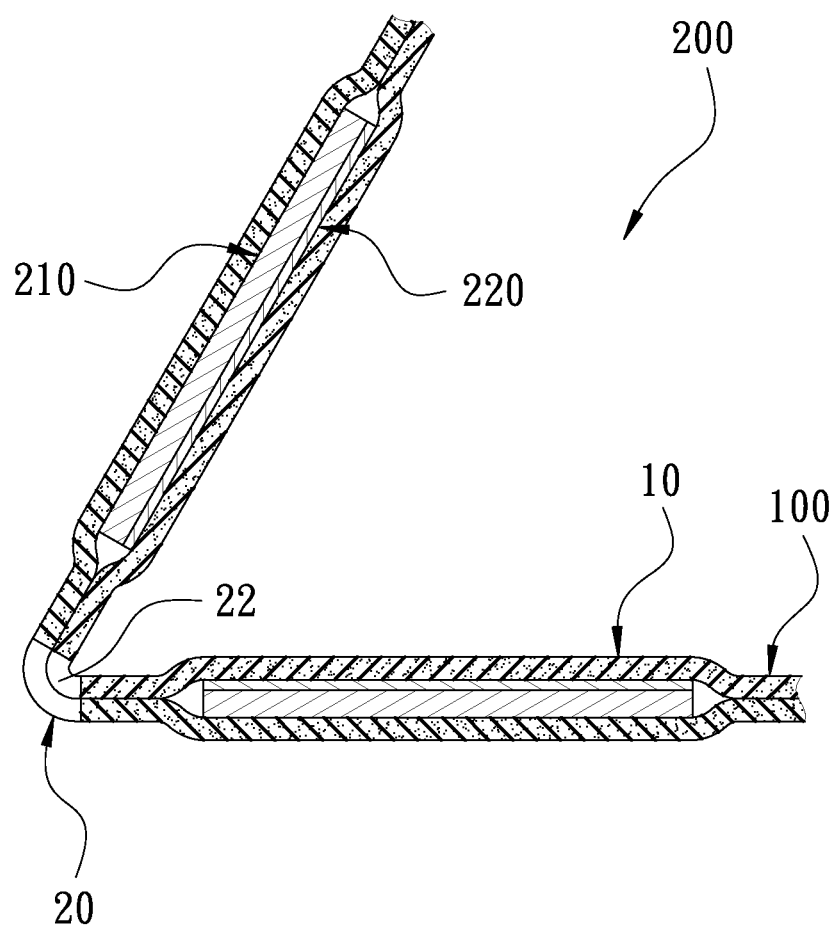
FIG. 9 is a sectional view according to the second embodiment of the present invention in a curved state.

Referring to FIG. 7 to FIG. 9, a second embodiment of the present invention is substantially similar to the first embodiment with the exceptions described hereinafter. The bending portions 20 are a plurality of spaced through holes 22 to provide a flexible and curved space, so that the fixing film 10 has the property of flexibility in the predetermined direction for the flexible chip set encapsulation structure 100 to have a good flexibility and that the chip set 200 can be curved freely.

Figure 10:
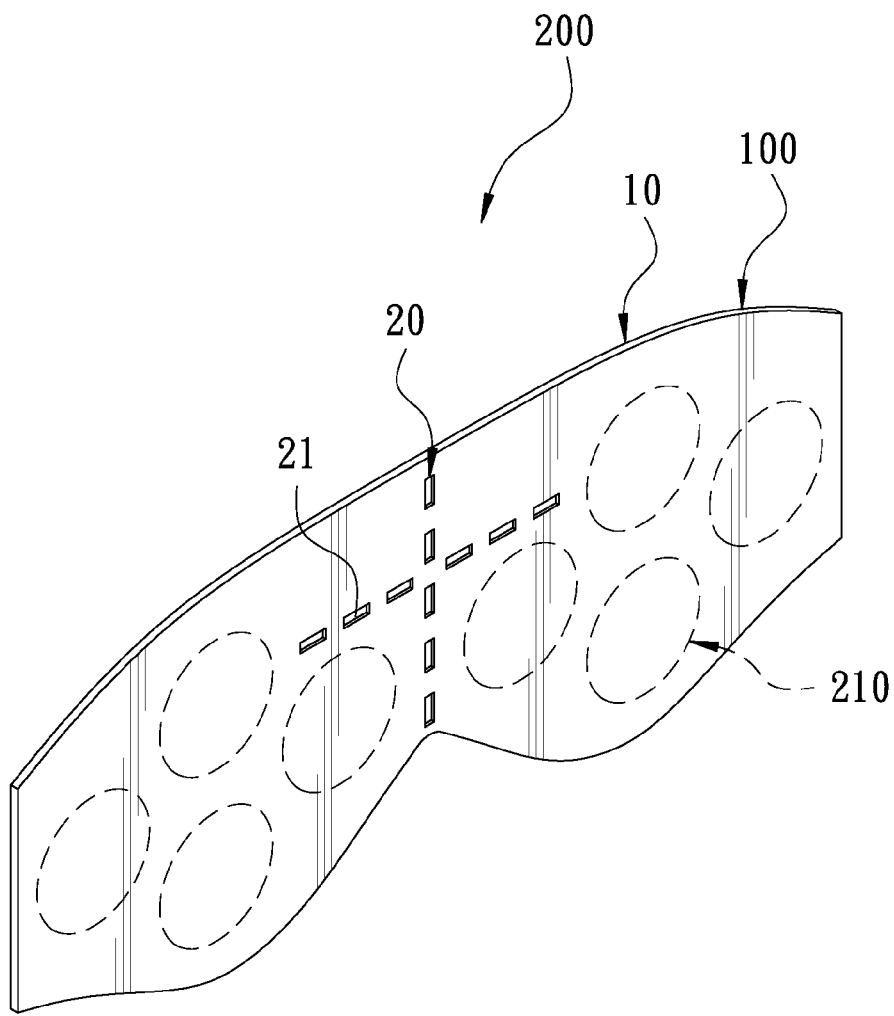
FIG. 10 is a perspective view according to a third embodiment of the present invention.

Referring to FIG. 10, a third embodiment of the present invention is substantially similar to the first embodiment with the exceptions described hereinafter. The chip set 200 is applied to an eyeshade. The chips 210 are arranged according to the position of the eyes and disposed at two sides of the fixing film 10. The fixing film 10 is gradually reduced from its two ends toward the middle portion. The middle portion of the fixing film 10 is formed with a plurality of bending portions 20 which are disposed crisscross at a predetermined position along the vertical direction and the transverse direction of the fixing film 10. In the third embodiment of the present invention, the bending portions 20 are spaced recesses 21 for the fixing film 10 to have a flexible and curved space. The fixing film 10 is flexible in a predetermined direction so that the fixing film 10 can be bent at a large angle freely at the position of the bending portions 20. Thus, when the chip set 200 cooperates with the eyeshade to be used, the flexible chip set encapsulation structure 100 is flexible along the contour of the eye portion. Thus, the chip set 200 is completely attached to the body. This provides a comfortable wear, and the chips 210 abut against the body to provide a better far infrared radiation effect.

Figure 11:
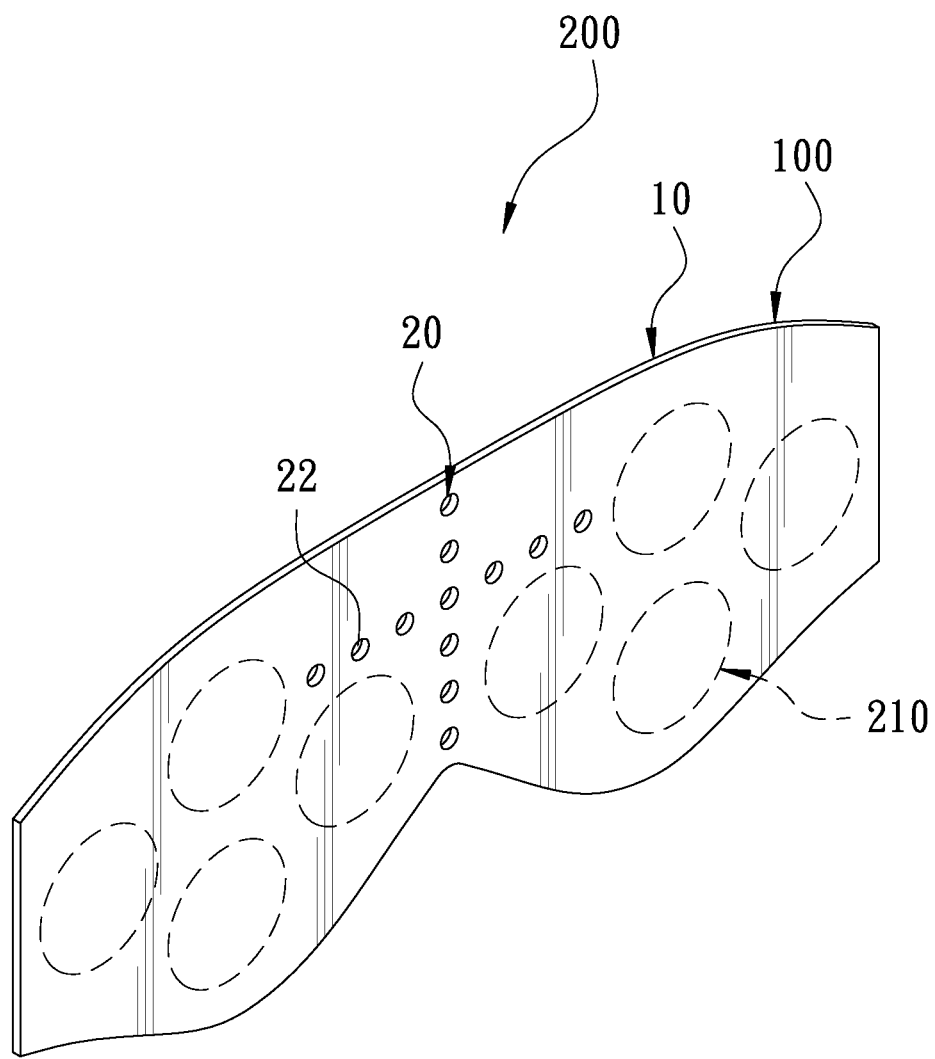
FIG. 11 is a perspective view according to a fourth embodiment of the present invention.

Referring to FIG. 11, a fourth embodiment of the present invention is substantially similar to the third embodiment with the exceptions described hereinafter. The bending portions 20 are a plurality of spaced through holes 22 to provide a flexible and curved space, so that the fixing film 10 has the property of flexibility in the predetermined direction for the flexible chip set encapsulation structure 100 to have a good flexibility and that the chip set 200 can be curved freely.

Figure 12:
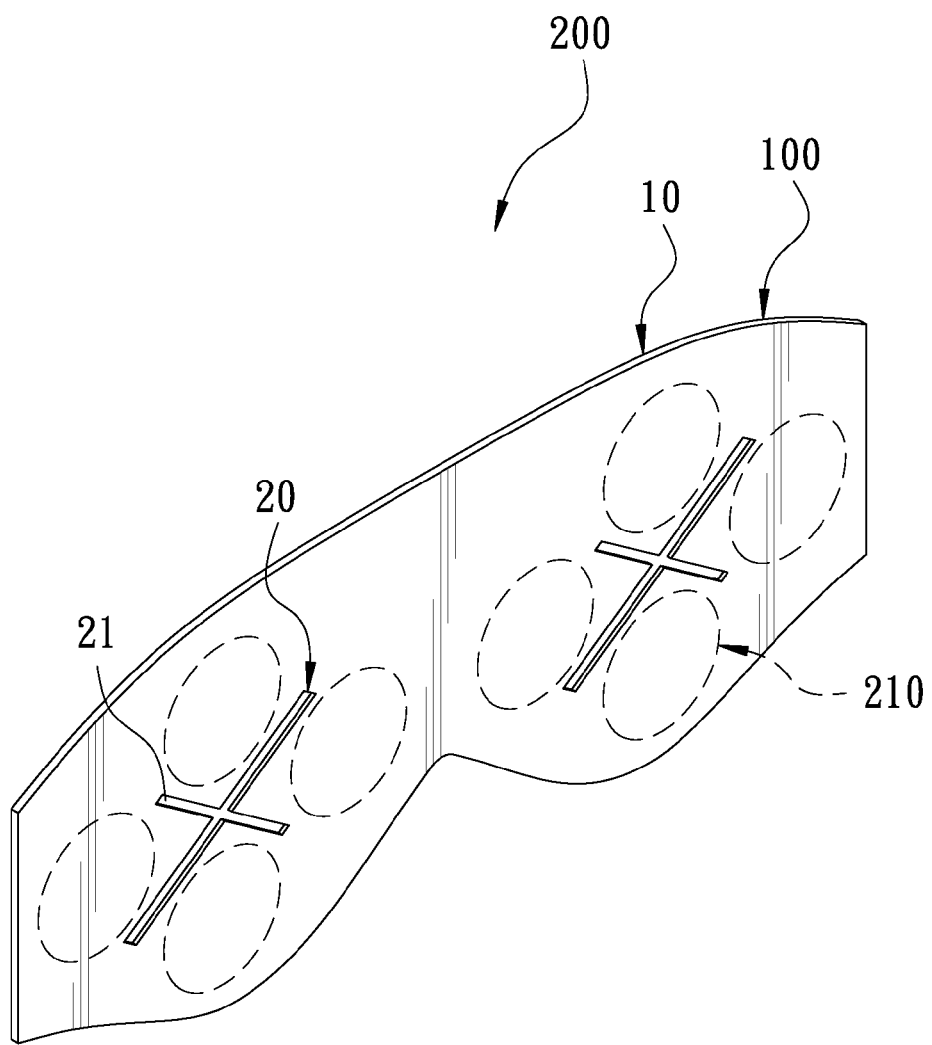
FIG. 12 is a perspective view according to a fifth embodiment of the present invention.

Referring to FIG. 12, a fifth embodiment of the present invention is substantially similar to the third embodiment with the exceptions described hereinafter. The bending portions 20 are crisscross disposed at the relative position between the chips 210 of the fixing film 10. Each bending portion 20 is a recess 21 to provide a flexible and curved space for the fixing film 10, so that the fixing film 10 has the property of flexibility in the predetermined direction for the flexible chip set encapsulation structure 100 to have a good flexibility and that the chip set 200 can be curved along the eye portion. Thus, the chip set 200 is completely attached to the body. This provides a comfortable wear, and the chips 210 abut against the body to provide a better far infrared radiation effect.

Figure 13:
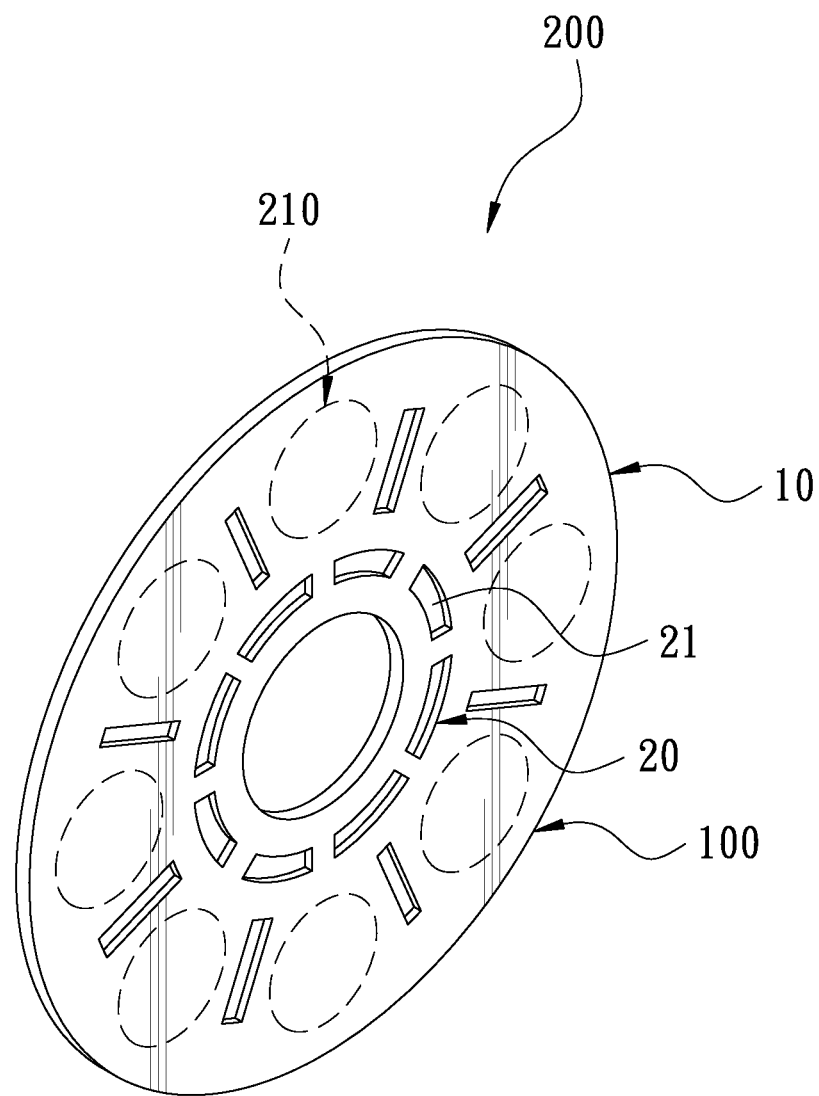
FIG. 13 is a perspective view according to a sixth embodiment of the present invention.

Referring to FIG. 13, a sixth embodiment of the present invention is substantially similar to the first embodiment with the exceptions described hereinafter. The chip set 200 is applied to a knee pad. The chips 210 are circularly arranged at an equal angle. The fixing film 10 is formed in a circle to wrap and fix the chips. The fixing film 10 has a plurality of spaced bending portions 20 disposed at a predetermined position along an inner circumferential portion thereof and between the chips 210. In the sixth embodiment of the present invention, the bending portions 20 are a plurality of spaced recesses 21 for the fixing film 10 to be bent flexibly, so that the fixing film 10 is flexible in a predetermined direction and the fixing film 10 can be bent freely at the position of the bending portions 20. Thus, when the chip set 200 cooperates with the knee pad to be used, the user can curve his/her knee freely, not limited to the flexible chip set encapsulation structure 100. The flexible chip set encapsulation structure 100 is flexible along the contour of the knee pad. Thus, the chip set 200 is completely attached to the body. This provides a comfortable wear, and the chips 210 abut against the body to provide a better far infrared radiation effect.

Figure 14:
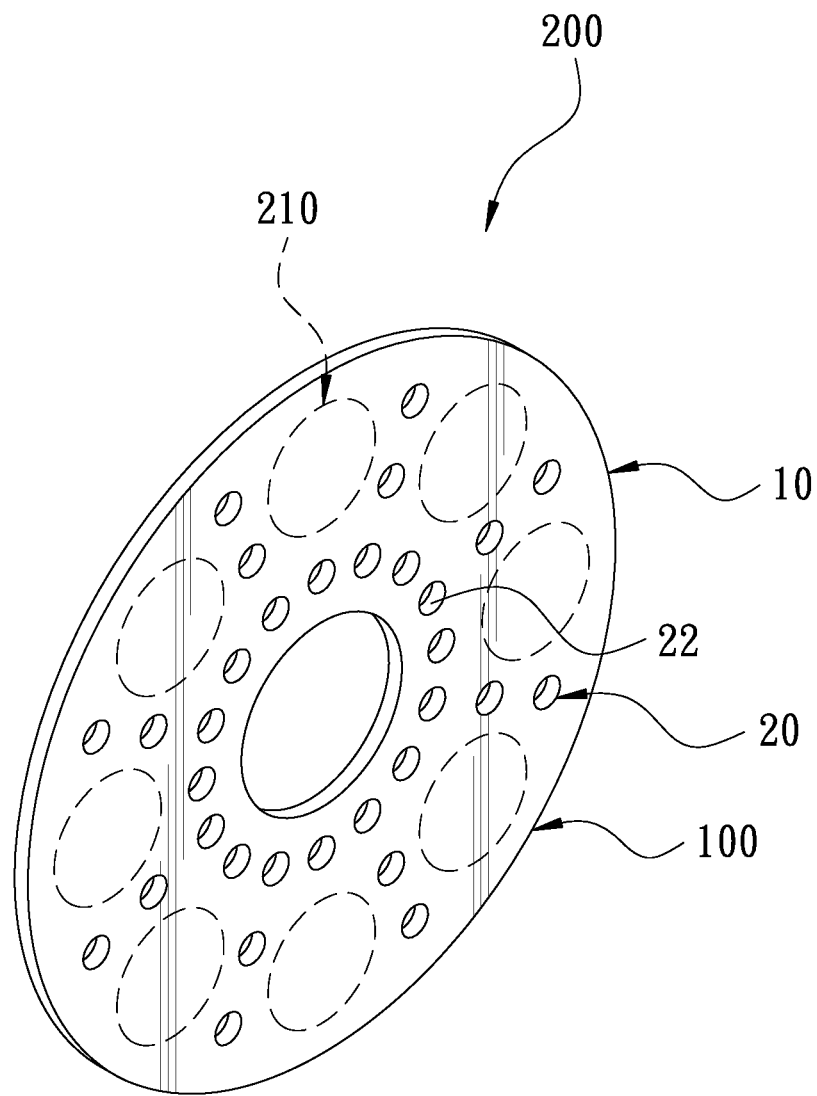
FIG. 14 is a perspective view according to a seventh embodiment of the present invention.

Referring to FIG. 14, a seventh embodiment of the present invention is substantially similar to the sixth embodiment with the exceptions described hereinafter. The bending portions 20 are a plurality of spaced through holes 22 to provide a flexible and curved space, so that the fixing film 10 has the property of flexibility in the predetermined direction for the flexible chip set encapsulation structure 100 to have a good flexibility and that the chip set 200 can be curved freely.

Although particular embodiments of the present invention have been described in detail for purposes of illustration, various modifications and enhancements may be made without departing from the spirit and scope of the present invention. Accordingly, the present invention is not to be limited except as by the appended claims.

What is claimed is:

1. A flexible chip set encapsulation structure, comprising:
   a chip set, the chip set comprising a plurality of spaced chips and a fixing film, the fixing film being adapted to wrap and fix the chips, the fixing film having at least one bending portion at a predetermined position; and
   the chips are circularly arranged at an equal angle, the fixing film being formed in a circle, the bending portion being disposed at an inner circumferential portion of the fixing film.

2. The flexible chip set encapsulation structure as claimed in claim 1, wherein the bending portion is disposed at a relative position between the chips of the fixing film.

3. The flexible chip set encapsulation structure as claimed in claim 1, wherein the chips are disposed at two sides of the fixing film, the bending portion being disposed at a middle portion of the fixing film.

4. The flexible chip set encapsulation structure as claimed in claim 1, wherein the bending portion is a recess.

5. The flexible chip set encapsulation structure as claimed in claim 1, wherein the bending portion is a plurality of spaced recesses.

6. The flexible chip set encapsulation structure as claimed in claim 1, wherein the bending portion is a plurality of spaced through holes.

* * * * *